United States Patent [19]

Uitti

[11] 4,009,218
[45] Feb. 22, 1977

[54] ALKYLAROMATIC HYDROCARBON DEHYDROGENATION PROCESS

[75] Inventor: Kenneth D. Uitti, Bensenville, Ill.

[73] Assignee: Universal Oil Products Company, Des Plaines, Ill.

[22] Filed: May 6, 1975

[21] Appl. No.: 574,986

[52] U.S. Cl. .......................................... 260/669 R
[51] Int. Cl.² .................. C07C 15/00; C07C 15/10
[58] Field of Search ................................ 260/669 R

[56] References Cited

UNITED STATES PATENTS

| 2,851,502 | 9/1958 | Bowman et al. | 260/669 R |
| 3,294,856 | 12/1966 | Huckins | 260/669 R |
| 3,492,222 | 1/1970 | vanTasseu | 208/321 |
| 3,515,765 | 6/1970 | Berger | 260/669 R |
| 3,515,766 | 6/1970 | Root et al. | 260/669 R |
| 3,515,767 | 6/1970 | Carson et al. | 260/669 R |
| 3,690,839 | 9/1972 | Jones | 260/669 R |
| 3,847,968 | 11/1974 | Hughes | 260/669 R |

FOREIGN PATENTS OR APPLICATIONS

| 1,301,874 | 1/1973 | United Kingdom | 260/669 R |

OTHER PUBLICATIONS

Handbook of Chem. & Phy. – 55th Ed. – p. C-494.
Condensed Chemical Dictionary – 8th Ed. – p. 673 (Hawley–Ep.).

Primary Examiner—Oscar R. Vertiz
Assistant Examiner—Eugene T. Wheelock
Attorney, Agent, or Firm—James R. Hoatson, Jr.; Robert W. Erickson; William H. Page, II

[57] ABSTRACT

Styrene is removed from a recycle water stream of an ethylbenzene dehydrogenation process by liquid-liquid extraction to prevent polymer buildup on heat exchange tubes and to lower coke formation in boiler tubes. The water stream is then fed into a heater to form steam for use within the reaction zone of the process. The solvent used for the extraction is benzene or a normal paraffin and preferably is the overhead product of a benzene-toluene column which separates the products of the process. The use of extraction lowers utility costs compared to stripping the recycle water stream.

3 Claims, 1 Drawing Figure

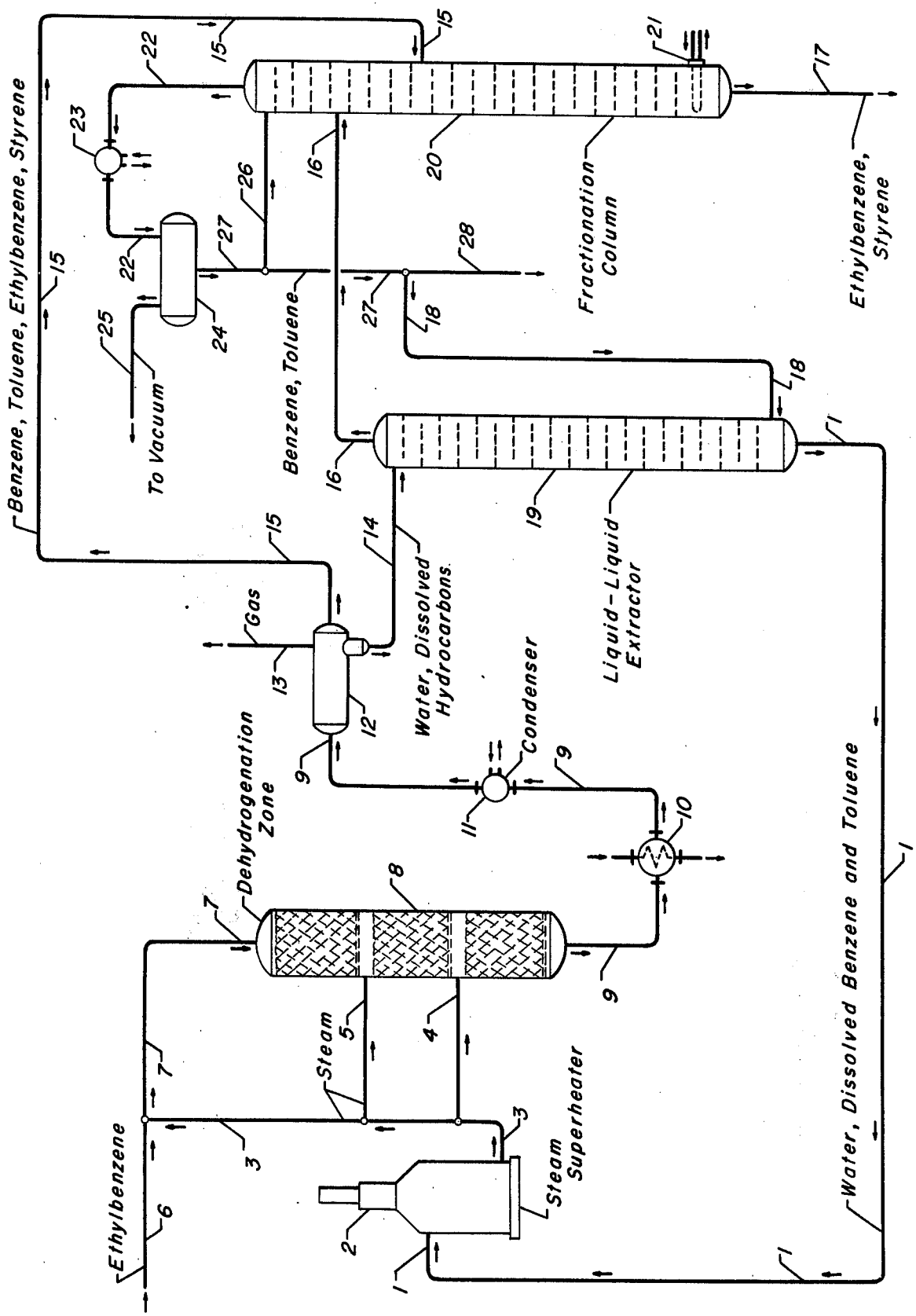

4,009,218

ALKYLAROMATIC HYDROCARBON DEHYDROGENATION PROCESS

FIELD OF THE INVENTION

The invention relates to a process for the catalytic dehydrogenation of alkylaromatic hydrocarbons wherein water is condensed from the reactor effluent and recycled for the production of superheated steam used within the reaction zone. The invention more specifically relates to a method of removing substantially all of an alkenylaromatic hydrocarbon, such as styrene, from the water by liquid-liquid extraction with a solvent, such as benzene.

DESCRIPTION OF THE PRIOR ART

The art of alkylaromatic hydrocarbon dehydrogenation is well developed as shown by the many commercial plants in operation and the wealth of literature in the field. Exemplary processes are shown in U.S. Pat. Nos. 3,515,765 and 3,515,766 (Cl. 260–699). Both of these references teach a process for the catalytic dehydrogenation of an alkylaromatic hydrocarbon, such as ethylbenzene, in which steam is passed through a reaction zone in admixture with the alkylaromatic hydrocarbon. The effluent of the reaction zone is cooled sufficiently to cause condensation of the water and heavier hydrocarbons. The effluent is then passed into a separator, and a water phase is removed and passed into a water stripper for the removal of hydrocarbons.

In the former reference, the water purified in the stripper is heat-exchanged with the reaction zone effluent to form steam used for stripping in a fractionation column. The steam is removed as an overhead vapor containing undehydrogenated hydrocarbons and returned to the reaction zone. In the latter reference, the stripped water is passed through a filter to remove hydrocarbons not removed in the stripper. It is recognized that the 0.01 to 0.08 mole percent of non-aromatic hydrocarbons in solution and in suspension will eventually foul heat-exchangers and boilers used to generate steam. The use of the filter therefore facilitates the passage of the stripped water into a fired feed heater.

U.S. Pat. No. 3,492,222 (Cl. 208–321) presents a solvent recovery method for use in a liquid-liquid extraction process. Non-aromatic hydrocarbons are removed from an aqueous wash stream by contacting the wash stream with an aromatic hydrocarbon. This is performed to avoid contamination of an aromatic extract by the non-aromatic hydrocarbons when this water is utilized to form the stripping steam used in separating the aromatic extract from a rich solvent.

BRIEF SUMMARY OF THE INVENTION

The invention provides a process for the dehydrogenation of alkylaromatic hydrocarbons wherein the utilities demand is reduced by passing the recycle water stream formed by condensing the effluent of a dehydrogenation zone through a liquid-liquid extraction zone to remove alkenylaromatic hydrocarbons. The water stream is then passed into a steam generation zone to form steam which is used in the dehydrogenation zone. The extraction operation is advantageously combined with the product fractionation zone by using the overhead product stream of the benzene-toluene column as the solvent stream used in the extraction zone and by returning the extract stream to the column as intermediate reflux material.

DESCRIPTION OF THE DRAWING

A stream of ethylbenzene and steam enters the process through line 6. It is then admixed with a first portion of superheated steam passing through line 3 to form a feed stream carried in line 7 and passed into a first catalyst bed within the dehydrogenation zone 8. The feed stream passes through a first bed of catalyst wherein the endothermic dehydrogenation reaction lowers the temperature of the reactants. A second portion of superheated steam carried through line 5 is therefore admixed with the effluent of the first catalyst bed to raise its temperature. The new admixture passes through a second bed of catalyst, and the effluent of this bed is then admixed with a third portion of steam passing through line 4. The effluent of the third catalyst bed leaves the dehydrogenation zone through line 9 and is passed through a heat-exchange means 10 wherein heat is recovered. The effluent stream continues in line 9 and passes through a condenser 11. This causes the separation of the effluent stream into a vapor phase and a liquid phase. These two phases pass through line 9 into a phase separator 12 wherein the liquid phase separates into a hydrocarbon phase and a water phase. The uncondensed vapors are removed from the phase separator through line 13, and the hydrocarbon phase is removed through line 15 and passed into a fractionation column 20. The water phase, which contains dissolved styrene and ethylbenzene, is removed through line 14 as a recycle water stream and passed into the top of a liquid-liquid extractor 19. The denser water phase passes downward through the extractor countercurrently to a solvent stream which enters the extractor through line 18.

Substantially all of the styrene which is dissolved in the entering water stream transfers into the solvent stream and is removed from the extractor in the extract stream removed in line 16. This extract stream is passed into the fractionation column 20 via line 16. The treated recycle water stream is removed from the bottom of the extractor through line 1 and now contains dissolved benzene but is free of styrene and ethylbenzene. This recycle water stream is passed into a steam superheater 2 to effect the formation of the steam carried in line 3.

In fractionation column 20, there is effected a separation of the hydrocarbon phase entering through line 15 into a hydrocarbon stream comprising a substantially pure mixture of toluene and benzene and a bottoms stream comprising styrene, ethylbenzene and tar. The heat for the separation is supplied through a reboiler 21, and the bottoms stream is removed through line 17. An overhead vapor stream is removed in line 22 and passed through a condenser 23. The resulting mixed-phase stream is passed into an overhead receiver 24. The uncondensed portions of the overhead vapor stream are removed through line 25 which is connected to a vacuum source. This source maintains the column at a subatmospheric pressure which reduces styrene polymerization by lowering the temperature required for the separation. A hydrocarbon stream is removed from the receiver as the overhead product. A first portion of this stream is returned to the column in line 26 as a reflux stream. The remaining portion passes through line 27, from which the solvent stream is withdrawn in line 18, and the net overhead product is removed in line 28.

DETAILED DESCRIPTION

Large amounts of styrene are produced commercially by the dehydrogenation of ethylbenzene. The dehydrogenation process is endothermic, and therefore the predominant processes for the production of styrene admix superheated steam with the ethylbenzene before it is fed into the reaction zone. The superheated steam acts as a heat source which allows a greater amount of dehydrogenation to be performed in the catalyst bed before the temperature becomes too low for the reaction to proceed. The effluent of the dehydrogenation zone is normally condensed to effect a separation of the hydrocarbons from the water. It is desirable to reuse the water which is separated by recycling the water to a steam generation zone. This latter term is intended to refer to any boiler or waste heat steam generator, etc., wherein liquid water is converted to steam. This recycling reduces the necessity of treating additional makeup water, and it also eliminates the problem of disposal of the condensed hydrocarbon-containing water.

The water which is removed from the separation zone will have dissolved in it a varying amount of the hydrocarbons present in the separator. It will therefore contain a mixture of various aromatic hydrocarbons, such as ethylbenzene, styrene, benzene and toluene and various polymeric compounds normally referred to as tar. It is recognized in the art that the styrene, ethylbenzene and tar must be removed before this water stream can be reused for the generation of steam. If this is not done, these materials will cause a severe coking problem in the tubes of the superheater causing a rapid shut-down of the process. Furthermore, the styrene forms a polystyrene coating on the surface of feed-effluent heat exchanger tubes. This tends to plug the exchanger and to reduce its heat transfer efficiency. The prior art therefore first strips the recycled water stream to remove substantially all of the lighter dissolved hydrocarbon materials. The stripped water is then often passed through a filtration system to remove the remaining hydrocarbons, especially the high-boiling tar which is not removed in the stripping operation. This filtration often comprises the passage of the water stream through a bed of activated charcoal. The stripping of the recycle water stream consumes a fair amount of energy and therefore increases the utility costs of the overall process.

It is an objective of this invention to provide a process for the dehydrogenation of ethylbenzene with reduced utility costs and wherein it is not necessary to strip this recycle water stream. The effluent of a dehydrogenation unit contains a large amount of low pressure steam which can be used for this (relatively low temperature) stripping operation, but cannot be used in the higher temperature hydrocarbon separations. For this reason, the invention is most useful in an integrated petrochemical complex wherein there exists a use for low pressure steam. One example is a benzene drying column on an alkylation unit producing the ethylbenzene fed to the dehydrogenation unit. Alternatively, the invention increases the amount of low pressure steam available for compression in steam conservation systems.

The present invention resides in the realization that the removal of all hydrocarbons from the recycle water stream is not necessary, and that the problems of polymer formation in heat exchangers and coke buildup in boiler tubes can be avoided in a less costly manner by simply displacing undesirable hydrocarbons in an extraction zone instead of removing hydrocarbons by stripping followed by filtration. It is only necessary to remove the $C_8$-plus alkylaromatic and alkenylaromatic hydrocarbons and tar. Benzene and toluene will normally pass through the boiler tubes unaffected, but can link up to form undesired biphenyls. Saturated cyclic compounds, paraffins and olefins will have a minimal detrimental effect as they tend to crack almost completely to methane and hydrogen in the presence of water. The present invention therefore comprises passing the water stream into a liquid-liquid extraction zone wherein substantially all of the undesired alkylaromatic and alkenylaromatic hydrocarbons are removed from the water stream by contact with a solvent stream comprising hydrocarbons having little or no tendency to obstruct the boiler tubes by coke formation. As used herein, the term "substantially all" indicates the removal of at least 90% and preferably 95% of the undesirable hydrocarbons. Likewise, the term "substantially free" is intended to indicate a molal percentage of less than 5% for the material referred to in the subject process stream. The concentration of dissolved benzene and toluene in the treated water will be fairly low and can be regulated by adjusting the temperature of the extraction zone.

The liquid-liquid extraction zone may take many forms. It may be a vertical extraction tower as shown in the drawing or a series of batch contacting operations comprised of mixing and settling zones. The extraction tower may use a rotating disk contactor or a pulsed mode of operation to promote extraction. The equipment and design considerations needed for the construction and operation of the zone are within the knowledge of those skilled in the art. Detailed information can be obtained from such references as section 14 of the fourth edition of *The Chemical Engineers' Handbook*, McGraw-Hill, 1963, or the series of articles on pages 50 to 104 of *Chemical Engineering Progress*, (Vol. 62, No. 9), Sept. 1966. Specifically, the size of the extraction zone and the required rate of the solvent stream are set by the composition and flow rate of the recycle water stream, the desired composition of the product water stream, the efficiency of the contactor and the solubilities of the various components in the two contacted streams.

As an example, to reduce the styrene concentration of a 380,000 lb./hr. water stream from 580 ppm. to 5.8 ppm. in an extraction zone equivalent to one theoretical stage and operated at 150° F. requires a benzene solvent stream of about 21,820 lbs./hr. The treated water stream would contain about 379,940 lbs./hr. of water, 960 lbs./hr. of benzene and 2 lbs/hr. of styrene. The exact conditions used in the extraction zone will be set after a consideration of the temperature effect on solubilities, the unadjusted temperature of the chosen input streams and the desired temperatures of the effluent streams. Extraction zones are normally run in a temperature range of from about 60° F. to about 200° F. and with a positive pressure ranging from about atmospheric to 200 psig. The pressure does not affect the extraction operation and is therefore chosen after a consideration of the pressure drop in the extractor, the cost of an extractor designed for a higher pressure and the volatility of the liquids.

From this example it may be seen that the benzene solvent stream required is smaller than the water stream. Therefore, even if the extract stream is fractionated to recover the styrene, the utilities cost is reduced due to the smaller amount and the lower latent heat of the benzene stream. The capital costs of using the invention should be no more than using a stripper. The structure of the stripper is very similar to an extraction column, but also includes a reboiler and possibly an overhead condenser. Depending on the ease of the extraction, it may possibly be performed in a number of low cost contacting and settling chambers. These reduced costs are two of the advantages of the invention.

The solvent stream used in the extraction zone may be any suitable liquid possessing a good solubility for styrene or other undesired hydrocarbons and which does not cause excessive coking in the heating tubes. The solvent stream may therefore comprise low molecular weight paraffinic hydrocarbons such as heptane, hexane, pentane or butane or a mixture of them. The solvent stream may also comprise benzene, and may therefore be a mixture of benzene and paraffinic hydrocarbons having from four to six carbon atoms per molecule. It is preferred that the solvent stream is a relatively pure benzene stream. In many instances, the ethylbenzene which is dehydrogenated in the styrene process is produced in an alkylation unit located in the same complex. The integration of these two processes is described in detail in U.S. Pat. No. 3,525,776. In just about all of these alkylation units a dragstream comprising benzene and non-aromatics is removed to prevent the buildup of the non-aromatics in the unit. This dragstream can be used advantageously as the solvent stream prior to being discharged from the process. It should first be treated as necessary for the removal of any water-soluble inorganic materials which would have an adverse effect if introduced into boiler tubes. In a boron trifluoride promoted benzene alkylation process, these materials are boron oxide hydrates which are typically removed by passing the dragstream through a bed of alumina.

The effluent of an ethylbenzene dehydrogenation process is typically separated in a fractionation zone such as described in U.S. Pat. No. 3,525,776. The hydrocarbonaceous phase removed from the phase separation or settling zone is passed into a first column referred to as a benzene-toluene column. This column is operated at a subatmospheric pressure to allow its operation at lower temperatures and hence reduce the rate of styrene polymerization. Various inhibitors such as elemental sulfur or 2,4-dinitrophenol are added for this same purpose. Sulfur is also introduced into the column by returning high molecular weight material separated from the bottoms stream of a styrene purification column. A more detailed description is contained in U.S. Pat. Nos. 3,476,656; 3,408,263; and 3,398,063. There is effected within the benzene-toluene column a separation of benzene and toluene from the effluent to produce an overhead stream which is substantially free of styrene and ethylbenzene. This stream contains preferably at least 95 mole percent benzene and toluene. It is an embodiment of this invention that this overhead stream is used as the solvent stream. It may also be further fractionated to produce a substantially pure benzene stream which can then be used as the solvent stream. The bottoms of the benzene-toluene column is passed into a second fractionation column from which ethylbenzene is removed as an overhead product and recycled. The bottoms stream of this column is purified to obtain the styrene.

The present invention may be applied to any process for the dehydrogenation of alkylaromatic hydrocarbons wherein the dehydrogenation zone effluent is condensed to form a liquid water phase and a portion of this water is to be recycled for the production of steam. The specific mode of operation of the reaction zone or the composition of the catalytic material is not determinative of the usefulness of the invention. The examples and description herein which refer specifically to the dehydrogenation of ethylbenzene are not intended to so limit the invention. This process may be applied to the dehydrogenation of other alkylaromatic hydrocarbons such as diethylbenzene, ethyltoluene, propylbenzene and isopropylbenzene and also to alkylaromatic hydrocarbons having other ring structures, including naphthalenes and anthracene compounds.

The reaction zone preferably comprises two or three beds of dehydrogenation catalyst with means for the intermediate addition and admixture of steam. Suitable systems are presented in U.S. Pat. Nos. 3,498,755; 3,515,763; and 3,751,232. The catalyst beds may be contained in separate reaction vessels and may have either a cylindrical or an annular shape. Different catalysts may be used in different beds as described in U.S. Pat. No. 3,223,743. Such catalysts generally consist of one or more metallic components selected from Groups VI and VIII of the periodic table. These metallic components are typically carried on a refractory inorganic oxide material such as alumina, silica, boria or mixtures thereof. One typical catalyst comprises 85% by weight ferric oxide, 2% chromia, 12% potassium hydroxide and 1% sodium hydroxide. A second typical catalyst comprises 90% by weight iron oxide, 4% chromia and 6% potassium carbonate. Methods for preparing suitable catalysts are well known in the art. This is demonstrated by the teachings of U.S. Pat. No. 3,387,053, wherein the manufacture is described of a catalytic composite of at least 35 wt.% iron oxide as an active catalytic agent, from about 1 to 8 wt.% zinc or copper oxide, about 0.5 to 50 wt.% of an alkali promoter, and from about 1 to 5 wt.% chromic oxide as a stabilizer and a binding agent. Catalysts preferably employed are available commercially and commonly referred to as "Shell 105" or "Shell 205".

Dehydrogenation conditions in general include a temperature of about 1000° F. to about 1800° F. and preferably about 1050° F. to about 1250° F. The temperature required for any specific unit will depend on the activity of the catalyst employed. The pressure maintained within the dehydrogenation zone is generally quite low and may range from about 0 to 100 psig., with a preferred pressure range being from about 2.0 to 10 psig. The feed stream is charged to the dehydrogenation zone at a liquid hourly space velocity, based on liquid hydrocarbon charge at 60° F., of about 0.1 hr.$^{-1}$ to about 1.0 hr.$^{-1}$, and preferably from 0.2 to 0.7 hr.$^{-1}$.

As previously mentioned, the alkylaromatic to be dehydrogenated is admixed with steam to counteract the temperature lowering effect of the dehydrogenation reaction. Preferably, steam is admixed with the feed stream and also added at intermediate points within the reaction zone. Some processes utilize indirect heat exchange of the reactants or heating elements within the catalyst bed. The steam and alkylaromatic hydrocarbon can be separately heated and commingled prior to contacting the reactants with the catalyst, or the steam and alkylaromatic can be first commingled and then heated. When ethylbenzene is being dehydrogenated, the space velocity, the rate of steam admixture and the inlet temperature are adjusted to result in the effluent of each catalyst bed having a temperature of about 1100° F. Preferably, steam is admixed with the feed stream to the dehydrogenation zone at a rate of about 0.65 to about 1.0 pound of steam per pound of ethylbenzene. A second portion is added to the effluent of the first catalyst bed at a rate of about 1.0 to about 1.2 pounds of steam per pound of effluent, and a third portion is added to the effluent of the second bed at a rate of about 0.8 to about 1.3 pounds per pound of effluent. These rates are adjusted such that the total effluent stream from the dehydrogenation zone will contain from about 3 to about 6 pounds of steam per pound of styrene.

The effluent stream removed from the dehydrogenation zone is often first heat exchanged for the dual purposes of lowering its temperature to prevent polymerization of the styrene and for the recovery of heat. The effluent stream may be heat exchanged against a make-up stream of steam, a reactant stream of this or another process or used as a heat source for fractionation. Commercially, the effluent stream is often passed through several heat exchangers for the heating of different streams. The reaction zone effluent may also be passed through a quench zone to rapidly cool it and lessen polymerization. The quench zone may be located after a heat exchange means as shown in U.S. Pat. Nos. 3,515,765 and 3,515,766, or the effluent stream may pass directly from the reactor into the quench zone as shown in U.S. Pat. No. 3,515,764. The cooling media fed to the quench zone is preferably liquid water removed from the phase separation zone. This water is not treated in the liquid-liquid extraction zone. The temperature of the effluent stream is finally lowered sufficiently to cause the condensation of essentially all of the hydrocarbons having 6 or more carbon atoms. The term "condensing zone" is therefore intended to refer to one or more of these operations, including at least one heat exchange, wherein the effluent stream of the reaction zone is cooled to a temperature at which a liquid phase is formed which contains at least 50 percent of the product material and water in the effluent stream. When large amounts of heat are recovered from the effluent stream, a trim cooler is sufficient to cool the effluent stream to the desired temperature of about 100° F.

The effluent stream is then passed into a phase separation zone wherein the effluent divides into a hydrocarbonaceous liquid phase, an aqueous liquid phase and a gaseous phase. There will be some water dissolved in the hydrocarbonaceous phase, which comprises ethylbenzene, styrene, benzene and toluene. There will also be some hydrocarbons dissolved in the aqueous liquid phase. The gaseous phase or vent gas stream will comprise hydrogen, methane, ethane, ethylene, carbon monoxide, carbon dioxide and other light gases which are formed in the process. The gaseous phase will separate from the liquid phase rather easily and is vented off. The liquid material is passed through a quiescent portion of the phase separation zone and the resulting liquid phases are separated by decantation. The design and operation of phase separation zones is well understood by those skilled in the art. For instance, U.S. Pat. No. 3,702,346 teaches the beneficial higher selectivity derived in a similar process by maintaining the product settler at a subatmospheric pressure, preferably in the range of from about 200 mm. Hg to about 600 mm. Hg absolute.

As an example of the preferred embodiment, which is the combination of liquid-liquid extraction of the recycle water stream with the operation of the effluent fractionation zone, a detailed description of the flows through a commercial three reactor ethylbenzene dehydrogenation unit are presented. The combined feed stream to the unit has a flow rate of 13,698 lbs./hr. and comprises a 637 B.P.S.D. (barrel per stream day) stream of fresh ethylbenzene and a 439 B.P.S.D. recycle ethylbenzene stream. After the addition of condensate, passage through the combined feed heat exchanger, the addition of steam and passage through a heater there is formed a 29,051 lbs./hr. feed stream for the first reactor which has a temperature of about 1125° F., a pressure of about 8 psig., and an average molecular weight of about 29.6. The effluent from the first reactor has an average molecular weight of about 28.8, a temperature of about 1020° F. and a pressure of about 6 psig. To this effluent there is added a 13,698 lbs./hr. stream of steam having a temperature of 1565° F. This forms a feed stream to the second reactor having a temperature of about 1170° F., a pressure of about 8 psig. and a flow rate of 42,749 lbs./hr. The effluent of the second reactor has a temperature of about 1080° F. and a pressure of about 6 psig. It is admixed with an 11,013 lbs./hr. stream of steam having a temperature of about 1530° F. to effect the formation of a 53,762 lbs./hr. feed stream for the third reactor, which has a temperature of about 1180° F. and an average molecular weight of about 22.2. The effluent of the third reactor has an average molecular weight of about 22, a temperature of about 1140° F. and a pressure of about 6 psig. These conditions will vary through the length of the run. For instance, the inlet temperature of the first reactor will vary from about 1100° F. to about 1125° F., and the inlet temperature of the third reactor will vary from about 1155° F. to about 1180° F. The weight hourly space velocities are about 0.6 in the first reactor, about 1.4 in the second reactor and about 2.0 in the third reactor. The catalysts used are known commercially as "Shell 105" and "CCI 97" catalysts.

The effluent of the dehydrogenation zone is heat exchanged with the combined feed stream and its temperature is reduced to about 435° F. A stream of about 5,500 lbs./hr. of 240° F. water is added to the effluent and lowers the effluent temperature to about 225° F. The quenched effluent is then admixed with a 100° F. hydrocarbon spillback stream derived from a settler and passed through a condenser which lowers its temperature to about 100° F. The effluent stream leaving the condenser has a flow rate of about 60,599 lbs./hr. and is passed into the settler. The vapor stream leaving the settler is passed through a chiller which reduces its temperature to about 40° F. The resulting condensation allows the return of the heavier hydrocarbons to the settler and produces an off-gas stream with an average molecular weight of about 6.2. A 14,705 lbs./hr. stream of the hydrocarbon phase is removed from the settler. Of this, about 1,377 lbs./hr. is used as the hydrocarbon spillback stream. This leaves a stream of about 13,368 lbs./hr. which is fed into a fractionation column referred to as the benzene-toluene column. This stream has an average molecular weight of about 104 and contains about 9 lbs. of dissolved gases and about 10 lbs. of dissolved water. A recycle water stream of about 45,254 lbs./hr. is removed from the water phase formed in the settler at about 100° F.

The feed stream enters the benzene-toluene column at a temperature of about 100° F. and a pressure of about 150 mm. Hg. absolute. The column may contain about 24 trays above the feed point and about 61 below the feed point. About 28 lbs./hr. of fresh sulfur and about 1,147 lbs./hr. of sulfur-containing tar derived from the styrene purification column are added with the feed stream to inhibit polymerization of the styrene. The operation of the column produces an overhead vapor stream of about 11,849 lbs./hr. at a temperature of about 115° F. and a pressure of about 100 mm. Hg absolute. Liquid material enters the reboiler at about 217° F. and a pressure of about 210 mm. Hg absolute. About 13,881 lbs./hr. of bottoms material having an average molecular weight of about 107.5 is removed and passed into an ethylbenzene column for recovery of the unconverted ethylbenzene for recycling. The bottoms of the ethylbenzene column is passed into a styrene column, from which a 6,891 lbs./hr. product stream is recovered.

The overhead condenser of the benzene-toluene column is operated so to produce a condensate having a temperature of 100° F. The effluent of the condenser includes about 9 lbs./hr. of gases which pass to the ejectors used to maintain the subatmospheric pressure within the column and about 10 lbs./hr. of water which is decanted from the overhead receiver. Normally, an 11,187 lbs./hr. reflux stream would be returned to the column and a 643 lbs./hr. net overhead product stream would be removed. The net overhead product comprises a relatively pure mixture of benzene and toluene which may be fractionated to provide pure benzene. By the method of the invention, a stream of about 2,700 lbs./hr. of the overhead material is diverted to a liquid-liquid extraction zone operated at a temperature of 100° F. and atmospheric pressure and used as the solvent stream used within the zone. Contact with the recycle water stream removed from the settler causes the transfer of about 24 lbs./hr. of styrene and ethylbenzene from the recycle water stream to the solvent stream. A hydrocarbon stream comprising essentially all of the original solvent stream, since the water stream was in equilibrium with hydrocarbons in the settler, is removed from the extraction zone as an extract stream. This stream is returned to the benzene-toluene column and used as reflux material fed to the column at an intermediate point due to its slightly lessened purity. This recovers the styrene and ethylbenzene removed from the recycle water stream. A very small amount of the recycle water stream, less than about 5 lbs./hr., transfers to the extract stream and the remaining portion forms a second water stream which is removed as the product of the extraction zone. This second water stream is recirculated for use in the reaction zone.

In accordance with this description, the preferred embodiment of the invention may be characterized as a process for the dehydrogenation of ethylbenzene, which comprises in cooperative combination the steps of admixing a feed stream comprising ethylbenzene with steam and contacting the resulting admixture with a dehydrogenation catalyst within a reaction zone maintained at dehydrogenation conditions and effecting the formation of an effluent stream comprising styrene, ethylbenzene and steam, effecting a partial condensation of the effluent stream by passage through a condensing zone, passing the effluent stream into a phase separation zone and effecting the formation of a hydrocarbonaceous phase comprising styrene, ethylbenzene, toluene and benzene and an aqueous phase comprising styrene, passing a first water stream comprising at least a portion of the aqueous phase into a liquid-liquid extraction zone and effecting a removal of substantially all of the styrene from the first water stream by contact with a solvent stream comprising benzene, and effecting the formation of a second water stream which is substantially free of styrene, passing at least a portion of the second water stream into a steam generation zone and effecting the formation of steam which is fed into the reaction zone, passing the hydrocarbonaceous phase into a fractionation zone and effecting a separation of the benzene and toluene from the styrene and ethylbenzene, and effecting therein the formation of a hydrocarbon stream which is substantially free of styrene and ethylbenzene, and passing at least a portion of the hydrocarbon stream into the liquid-liquid extraction zone as the solvent stream.

I claim as my invention:

1. A process for the dehydrogenation of ethylbenzene which comprises in cooperative combination the steps of:

a. admixing a feed stream comprising ethylbenzene with steam and contacting the resulting admixture with a heterogeneous fixed-bed dehydrogenation catalyst within a reaction zone maintained at dehydrogenation conditions and effecting the formation of an effluent stream comprising styrene, ethylbenzene and steam;

b. effecting a partial condensation of the effluent stream by passage through a condensing zone;

c. passing the effluent stream into a phase separation zone and effecting the formation of a hydrocarbonaceous phase comprising styrene, ethylbenzene, toluene and benzene and an aqueous phase comprising styrene;

d. passing a first water stream comprising at least a portion of the aqueous phase into a liquid-liquid extraction zone and effecting a removal of substantially all of the styrene from the first water stream by contact with a solvent stream comprising benzene, and effecting the formation of a second water stream which is substantially free of styrene;

e. passing at least a portion of the second water stream into a steam generation zone and effecting the formation of steam which is fed into the reaction zone;

f. passing the hydrocarbonaceous phase comprising styrene, ethylbenzene, toluene and benzene into a fractionation zone and effecting a separation of the benzene and toluene from the styrene and ethylbenzene, and effecting therein the formation of a solvent stream comprising benzene which is substantially free of styrene and ethylbenzene; and, g. passing at least a portion of the solvent stream comprising benzene into the liquid-liquid extraction zone as the solvent stream.

2. The process of claim 1 further characterized in that an extract stream comprising benzene, toluene and styrene and which is removed from the liquid-liquid extraction zone is passed into a fractionation column from which the solvent stream comprising benzene is removed as an overhead product stream.

3. The process of claim 2 further characterized in that said solvent stream contains at least 90 mole percent benzene and toluene.

* * * * *